US012765772B2

(12) United States Patent
Beder

(10) Patent No.: US 12,765,772 B2
(45) Date of Patent: Oct. 20, 2026

(54) OPHTHALMIC LOUPE, LENS COMBINATION AND OPTICAL IMAGING SYSTEM

(71) Applicant: Carl Zeiss Meditec AG, Jena (DE)

(72) Inventor: Christian Beder, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 251 days.

(21) Appl. No.: 18/628,708

(22) Filed: Apr. 6, 2024

(65) Prior Publication Data

US 2024/0341595 A1 Oct. 17, 2024

(30) Foreign Application Priority Data

Apr. 14, 2023 (DE) ..................... 10 2023 109 456.4

(51) Int. Cl.

| | |
|---|---|
| ***G02B 21/00*** | (2006.01) |
| ***A61B 3/12*** | (2006.01) |
| ***A61B 3/13*** | (2006.01) |
| ***A61B 3/14*** | (2006.01) |
| ***G02B 13/18*** | (2006.01) |

(52) U.S. Cl.

CPC .................. *A61B 3/13* (2013.01); *A61B 3/12* (2013.01); *A61B 3/14* (2013.01); *G02B 13/18* (2013.01); *G02B 21/0012* (2013.01)

(58) Field of Classification Search

CPC .... A61B 3/13; A61B 3/12; A61B 3/14; G02B 13/18; G02B 21/0012; G02B 25/002; G02B 27/0025

See application file for complete search history.

(56) References Cited

U.S. PATENT DOCUMENTS 3,953,111 A * 4/1976 Fisher ..................... G02B 13/08 359/770
4,307,944 A * 12/1981 Schirmer ............ A61F 9/00821 606/4

(Continued)

FOREIGN PATENT DOCUMENTS

DE 102017105580 A1 5/2018

OTHER PUBLICATIONS

Toslak et al., "Trans-pars-planar illumination enables a 200° ultra-wide field pediatric fundus camera for easy examination of the retina", Research Article in Biomedical Optics Express, Dec. 5, 2019, pp. 68-76, vol. 11, Issue No. 1, https://doi.org/10.1364/BOE.11.000068, Optical Society of America, University of Illinois at Chicago, Chicago, IL 60607, USA.

(Continued)

*Primary Examiner* — Bumsuk Won
*Assistant Examiner* — John C Sipes
(74) *Attorney, Agent, or Firm* — Ewers IP Law PLLC; Falk Ewers

(57) ABSTRACT

An ophthalmic loupe for generating an aerial image of a portion of an eye is provided. The ophthalmic loupe includes at least one lens, which in turn includes at least one aspheric lens face. In combination with the remaining lens faces, the at least one aspheric lens face generates an aerial image of the portion of the eye with a field of view with a negative distortion in its outer region. In this case, the absolute value of the negative distortion at the edge of the field of view is larger than 15%.

18 Claims, 6 Drawing Sheets

(56) References Cited

U.S. PATENT DOCUMENTS

| | | | | | |
|---|---|---|---|---|---|
| 4,738,521 | A * | 4/1988 | Volk | A61B 3/12 | 359/708 |
| 4,934,771 | A * | 6/1990 | Rogers | G02B 23/12 | 359/356 |
| 5,436,680 | A | 7/1995 | Volk | | |
| 5,652,639 | A * | 7/1997 | Patel | A61B 3/132 | 351/200 |
| 7,768,715 | B2 * | 8/2010 | Gohman | G02B 15/1435 | 359/689 |
| 10,842,374 | B2 | 11/2020 | Hogele et al. | | |
| 2006/0227415 | A1 * | 10/2006 | Caldwell | G02B 7/008 | 359/432 |
| 2017/0322493 | A1 * | 11/2017 | Sun | G03F 7/70641 | |
| 2018/0141153 | A1 * | 5/2018 | Högberg | B23K 26/064 | |
| 2019/0076019 | A1 * | 3/2019 | Farberov | G02B 3/04 | |
| 2021/0315662 | A1 * | 10/2021 | Freeman | G06F 3/012 | |
| 2022/0095912 | A1 * | 3/2022 | Williamson | G02B 7/14 | |
| 2022/0387127 | A1 * | 12/2022 | Kao | G01N 21/6458 | |

OTHER PUBLICATIONS

Chalam et al., “Refractions and Reflections—Optics of Wide-Angle Panoramic Viewing System-Assisted Vitreous Surgery”, Survey of Ophthalmology, Jul.-Aug. 2004, pp. 437-445, vol. 49, Issue No. 4, Elsevier Inc., Department of Ophthalmology, University of Florida College of Medicine, Jacksonville, Florida, US.

Office Action issued in German Patent Application No. DE 10 2023 109 456.4 (from which this application claims priority), dated Dec. 13, 2023 and English language translation thereof.

* cited by examiner

OPHTHALMIC LOUPE, LENS COMBINATION AND OPTICAL IMAGING SYSTEM

CROSS REFERENCE TO RELATED APPLICATIONS

This application claims priority to German patent application DE 10 2023 109 456.4, filed Apr. 14, 2023, the entire content of which is incorporated herein by reference.

TECHNICAL FIELD

The present disclosure relates to an ophthalmic loupe. In addition, the disclosure relates to a lens combination with an ophthalmic loupe. Moreover, the disclosure relates to an optical imaging system with a surgical microscope and an ophthalmic loupe.

BACKGROUND

So-called contactless visualization systems are frequently used for ophthalmic surgery on the posterior segment, and these have started to take over from the erstwhile visualization with a contact glass placed on the patient's eye. These systems operate with so-called ophthalmic loupes, which are placed just above the patient's eye and supply a real (albeit inverted) aerial image of the eye fundus in an intermediate image plane, and said image is then observed in turn using a surgical microscope.

An example of an ophthalmic loupe is described in U.S. Pat. No. 5,436,680, and an example of a lens combination with an ophthalmic loupe is described in DE 10 2017 105 580 A1.

Although ophthalmic loupes should usually keep all optical aberrations within the field of view of the aerial image to a minimum, a distortion of up to 15% at the edge of the field of view is allowed for the ophthalmic loupe described in U.S. Pat. No. 5,436,680, in order to give an impression of the curvature of the eye fundus in the image.

In the context of ophthalmic loupes, it is desirable, as a matter of principle, to image as much of the retina as possible in order to provide the physician with an overview that is as complete as possible and in order to avoid indentations (the physician makes an indentation in the eye from the back using an instrument, i.e., presses said eye inward in order to view the edge of the retina). However, currently used ophthalmic loupes do not have a field of view able to display an object field which even comes close to the ora serrata (the edge of the retina). Thus, only part of the retina is imaged at any one time, and the physician needs to make an indentation in the eye by mechanical means in order to be able to inspect or treat the entire retina. One reason for this is that it becomes ever more difficult to correct the optical aberrations of an ophthalmic loupe as the field of view becomes larger.

SUMMARY

It is therefore an object of the present disclosure to provide an ophthalmic loupe, a lens combination having an ophthalmic loupe, and also an optical imaging system having a surgical microscope and an ophthalmic loupe, with which it is possible to represent an object field that comes close to the ora serrata and ideally contains the ora serrata in the field of view.

The aforementioned object is achieved by an ophthalmic loupe, by a lens combination, and by an optical imaging system as described herein.

An ophthalmic loupe according to an aspect of the disclosure for generating an aerial image of an object field of an eye includes at least one lens and at least two lens faces. At least one of the lens faces is an aspheric lens face. In combination with the remaining lens face or the remaining lens faces, the at least one aspheric lens face generates an aerial image of the object field of the eye with a field of view with a negative distortion, i.e., a barrel distortion, in its outer region. The absolute value of the negative distortion at the edge of the field of view is larger than 15%, typically larger than 18% and in particular larger than 20%. In the process, the areal image is generated on the side of the ophthalmic loupe facing away from the eye.

The negative distortion at the edge of the field of view leads to representations of regions of the object field imaged at said edge of the field of view being smaller in comparison with representations of regions of the object field imaged in central regions of the field of view. In this case, the absolute value of the negative distortion specifies the percentage by which a radial length element of the object field in the field of view has been compressed in comparison with a corresponding length element in a non-distorted field of view. In the case of a positive distortion, i.e., a pincushion distortion, a radial length element of the object field in the distorted field of view would be stretched in comparison with a corresponding radial length element in the non-distorted field of view. On account of the compression, the negative distortion leads to outer regions of the imaged object field in the field of view being moved closer to the center of the field of view. As a consequence, a larger object field can be imaged in the field of view. If a significantly large negative distortion is allowed at the edge of the field of view, i.e., a negative distortion larger than 15%, typically larger than 18% and in particular larger than 20%, it is thus possible to provide an ophthalmic loupe which can image a very large object field, i.e., an object field which covers a very large angular range. In this case, a very large object field covers an angular range with half an opening angle of 45° or more, typically an angular range with half an opening angle of 48° or more, and in particular an angular range with half an opening angle of 52° or more.

It is advantageous if no more than two aspheric lens faces are present in the ophthalmic loupe according to an aspect of the disclosure. This can keep the manufacturing outlay for the ophthalmic loupe relatively low. If further lens faces are present in addition to the no more than two aspheric lens faces, then these further lens faces are spherical lens faces which can be produced with less outlay. Moreover, if two aspheric lens faces are present, it is advantageous if these two aspheric lens faces are present on the same lens because only a single aspheric lens needs to be produced in that case.

Hence, the disclosure relies on the use of a significant aberration, specifically a large distortion, to achieve the aforementioned object. There is no risk of negative consequences of this significant distortion in the edge region of the field of view since the retina, as observation object, has no rectangular structures in the object field with which the distortion might be identified. Additionally, since the surgical instruments are subject to the same distortion in the image as the retina, this also ensures that the physician always strikes the intended point with the surgical instrument.

In order to bring the edge of the object field in the field of view closer to the center of the field of view without the edge regions of the object field being represented too small, it is advantageous if the at least one aspheric lens face, in combination with the remaining lens face or the remaining lens faces, generates an aerial image in which at least the outer 40%, typically at least the outer 50%, of the field of view has a negative distortion. If the negative distortion were to start only further to the outside in the field of view, then the negative distortion at the edge would have to be particularly large so that the edge of the imaged object field can be moved close enough to the center of the field of view in order to accommodate the desired very large angular range of the object in the field of view. However, since a large negative distortion at the edge of the field of view is also accompanied by a significant compression of the structures in the object field imaged at the edge of the field of view, it might be the case that, if a negative distortion is too large, small structures in the object field imaged at the edge of the field of view are no longer represented with the necessary recognizability for the physician. If at least the outer 40%, typically the outer 50%, of the field of view has a negative distortion, then the maximum negative distortion at the edge of the field of view can be limited to an absolute value of below 30% and ideally to an absolute value of below 25%, in order to ensure recognizability of even small structures in the object field at the edge of the field of view.

Moreover, it is advantageous if the at least one aspheric lens face, in combination with the remaining lens face or the remaining lens faces, generates an aerial image in which at most the innermost 60%, typically at most the innermost 50%, of the field of view has no distortion or a positive distortion, with the positive distortion having an absolute value of less than 0.75%, typically less than 0.60% and ideally less than 0.55%. Within the scope of the present disclosure, negative distortions not exceeding a value of 0.3% should also be considered to be no distortion. If a noticeable positive distortion were present in the inner region of the field of view, then this would lead to a stretching of radial distances between structures in the object field imaged in the interior of the field of view, and this in turn would lead to the edge of the field of view requiring a larger compression of the structures in the object field imaged there in order to accommodate the desired very large angular range of the object field in the field of view. This might also lead to structures in the object field imaged at the edge of the field of view requiring such a significant reduction in size that they can no longer be represented with the required recognizability for the physician. Such a situation can be avoided by limiting the positive distortion in the innermost 60%, typically at most the innermost 50%, of the field of view to a maximum positive distortion of less than 0.75%.

In order to harmoniously adapt the inner field of view region, where there is neither a compression nor a stretching of the structures in the object field imaged there, or in which there is at most an unnoticeable stretching of the structures in the object field imaged there, to the outer field of view region, in which there is a noticeable compression of the structures in the object field imaged there, it is advantageous if the at least one aspheric lens face, in combination with the remaining lens face or the remaining lens faces, leads to a negative distortion which, at least in the outer 40% of the field of view, typically at least in the outer 50% of the field of view, increases more than proportionally in the direction of the edge of the field of view. This measure can create a "smooth" transition between the inner field of view region and the outer field of view region for the observer. By contrast, without this measure the field of view would contain a transition region in which there is a sudden compression of structures in the object field imaged in the field of view. For example, if a physician were to move a surgical instrument through this transition region, then the representation of the instrument would experience a sudden compression during the movement through the transition region, and this may irritate the physician. A sudden compression can be avoided by the more than proportional increase in the negative distortion. In order to particularly harmoniously adapt the transition between the inner field of view region, where there is neither a compression nor a stretching of the structures in the object field imaged there, or in which there is at most an unnoticeable stretching of the structures in the object field imaged there, to the outer field of view region, in which there is a noticeable compression of the structures in the object field imaged there, the at least one aspheric lens face, in combination with the remaining lens face or the remaining lens faces, can in particular lead to a distortion which, in the outer 40% of the field of view, typically in the outer 50% of the field of view, can be described by a polynomial P(r) whose second derivative, for example within the scope of a linear regression, can be approximated by a straight line with a coefficient of determination of at least R2≥99%, typically with a coefficient of determination of at least R2≥99.9%. Here, "r" describes the distance of a field point in the field of view from the center of the field of view, normalized to the maximum radius of the field of view. In particular, the second derivative being able to be approximated by a straight line with a coefficient of determination of at least R2≥99%, typically at least R2≥99.9%, can be achieved by virtue of the polynomial P(r) not having any term with a power larger than 3. Should the polynomial P(r) nevertheless have terms with a power larger than 3, the coefficients of these terms must be so small that the second derivative of the polynomial P(r) can be approximated by a straight line with a coefficient of determination of at least R2≥99% and typically of at least R2≥99.9%.

The ophthalmic loupe according to an aspect of the disclosure can be configured as a lens system including at least two lenses. Compared with the use of a single lens, the use of at least two lenses offers design advantages to the effect either that work can be carried out with smaller radii of curvature of the lens faces in the case of the same very large angular range of imaging as for an individual lens or that the angular range usable for the imaging is increased in the case of similar radii of curvature as for an individual lens. Moreover, the combination of at least two lenses offers the possibility of configuring the ophthalmic loupe to be achromatic.

However, it is also advantageous if the ophthalmic loupe according to an aspect of the disclosure is configured as a lens system including no more than three lenses since each additional lens increases the installation length of the system along its optical axis and consequently makes the arrangement thereof between the patient's eye and the surgical microscope more difficult.

If the ophthalmic loupe is configured as a lens system constructed from a plurality of lenses, said lens system includes a first lens configured to form the eye-side end of the lens system when the ophthalmic loupe is used and a second lens configured to form the aerial image-side end of the lens system when the ophthalmic loupe is used. In that case, the first lens includes a first lens face facing the eye when the ophthalmic loupe is used, and the second lens includes a second lens face forming the last lens face in front of the aerial image when the ophthalmic loupe is used. In this context, it is advantageous if the first lens face has a radius of curvature of at least 100 mm, and/or the second lens face has a radius of curvature of at least 100 mm. In the case of the first lens face, it is even advantageous for the latter to have a radius of curvature of at least 200 mm in this context. In the process, a large radius of curvature leads to a relatively flat lens face, whereby it is possible to avoid the situation where, if the first lens face is configured as a concave lens face, the first lens face facing the eye attaches itself to the eye in the case of inadvertent contact with the eye. Moreover, it is possible to avoid the situation where, if the second lens face is configured as a concave lens face, contamination or liquids impairing the visualization of the eye collect on the last lens face in front of the aerial image during the treatment or the examination of the eye.

In an advantageous configuration of the ophthalmic loupe, the latter has a refractive power of at least 90 diopters so the aerial image is located as close as possible to the ophthalmic loupe such that, when a surgical microscope is used to observe the aerial image, its working distance or its front focal distance need not be modified too much.

The disclosure also provides a lens combination to be arranged between the main objective of a surgical microscope and an eye. The lens combination includes an ophthalmic loupe according to an aspect of the disclosure, which should face the eye and which generates an aerial image of a portion of the eye in an intermediate image plane, and an optical group, which should face the main objective. The optical group is configured to displace the focus of the main objective into the intermediate image plane. In addition or in an alternative, the optical group can also be configured to compensate for chromatic aberrations of the ophthalmic loupe. In this case, the optical group may include one lens or a plurality of lenses.

According to an aspect of the disclosure, an optical imaging system is also provided, the latter including a surgical microscope with an observation beam path and a focus of the observation beam path, and also an ophthalmic loupe according to an aspect of the disclosure. In the optical imaging system according to an aspect of the disclosure, the ophthalmic loupe is introducible into the observation beam path of the surgical microscope such that the aerial image of the ophthalmic loupe is located at the focus of the observation beam path. In this case, the ophthalmic loupe can be part of a lens combination according to an aspect of the disclosure in particular. Such an optical imaging system enables the magnified observation of the posterior segment of the eye, wherein it is also possible to observe a very large object field on account of the configuration according to an aspect of the disclosure of the ophthalmic loupe. In this case, the magnified observation is implemented by virtue of the aerial image being magnified by the surgical microscope.

BRIEF DESCRIPTION OF THE DRAWINGS

The disclosure will now be described with reference to the drawings wherein.

DESCRIPTION OF EXEMPLARY EMBODIMENTS

Figure 1:
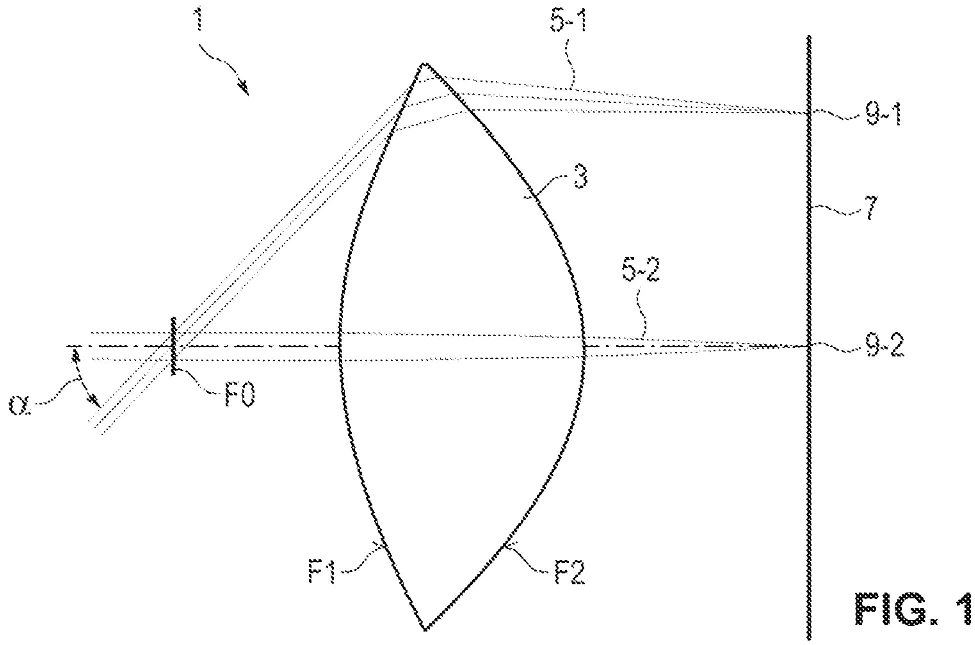
FIG. 1 shows an exemplary embodiment of an ophthalmic loupe including a single lens.
Figure 2:
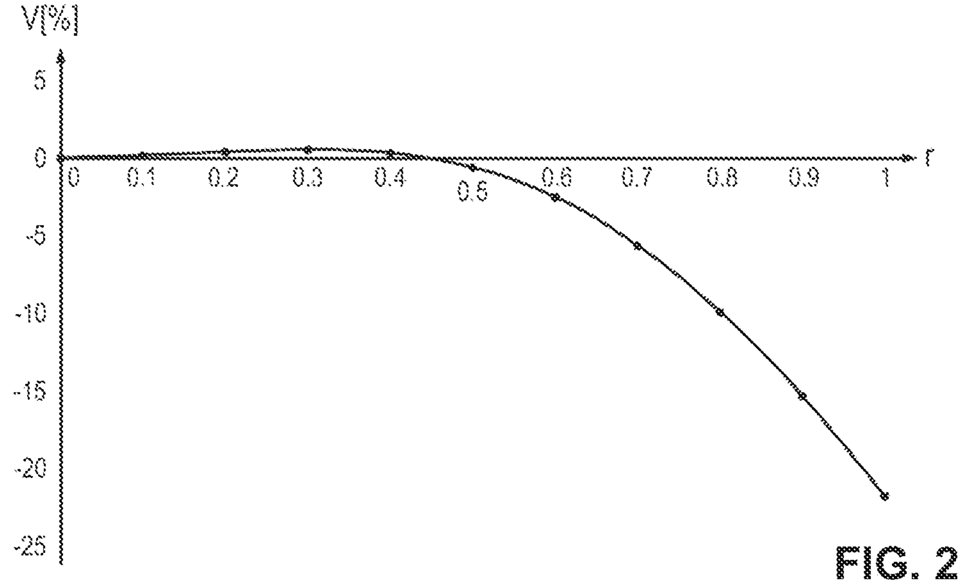
FIG. 2 shows, in the form of a diagram, the percentage distortion in the field of view generated by the ophthalmic loupe from FIG. 1, as a function of the distance from the center of the field of view.
Figure 3:
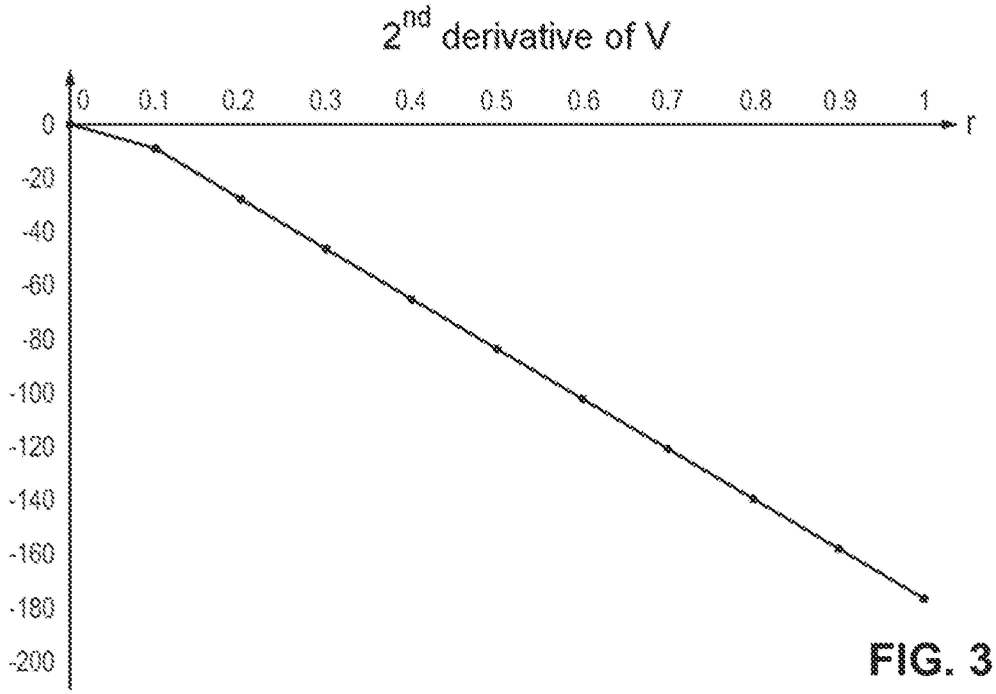
FIG. 3 shows, in the form of a diagram, the second derivative of the percentage distortion in the field of view generated by the ophthalmic loupe from FIG. 1, as a function of the distance from the center of the field of view.

An ophthalmic loupe 1 according to a first exemplary embodiment of the disclosure will be described below with reference to FIGS. 1 to 3. In this exemplary embodiment, the ophthalmic loupe 1 includes merely a single lens 3 with a first lens face F1, which should face the eye (not depicted here) when the ophthalmic loupe 1 is used, and a second lens face F2, which forms the last lens face in front of the image plane 7 in which the aerial image is created. The two lens faces F1 and F2 are aspheric faces in the present exemplary embodiment. The basic radii of curvature R of the two faces F1 and F2, their distances from the next face or from the image plane 7, the glass material and the face diameters are summarized in Table 1. The face F0 represents an imaginary face through which all imaging beams pass. In practice, this face corresponds to the pupil illuminated within the scope of the examination or treatment of the eye.

TABLE 1

| Face | Basic radius of curvature R [mm] | Distance [mm] | Material | Diameter [mm]: |
|---|---|---|---|---|
| F0 | inf | 6.3 | | 1 |
| F1 (ASP) | 13.280 | 9.219 | L-BSL7 (Ohara) | 19.9 |
| F2 (ASP) | −7.534 | 8.328 | | 20.4 |

The aspheric faces can be represented by the following equation:

$$z(r)=\frac{r^2}{R\left(1+\sqrt{1-(1+k)\frac{r^2}{R^2}}\right)}+a_4r^4+a_6r^6+a_8r^8+a_{10}r^{10}$$

Here, z(r) specifies the distance of a surface point on the aspheric face, which is situated at the radial distance r from the lens vertex, from a tangential plane, which is tangential to the lens vertex, in the direction perpendicular to the tangential plane. In this equation, R represents the basic radius of curvature of the face, k represents the conic constant and r represents the radial distance from the lens vertex. The parameters a4, a6, a8, and a10 are referred to as asphere coefficients and, together with the basic curvature R and the conic constant k, characterize the aspheric face. The asphere coefficients a4, a6, a8, and a10 and the conic constant are specified in Table 2 for the aspheric lens faces F1 and F2.

TABLE 2

| Face | k | a4 | a6 | a8 | a10 |
|---|---|---|---|---|---|
| F1 (ASP) | −4.131E+00 | 0 | 0 | 0 | 0 |
| F2 (ASP) | −7.807E−01 | 4.046E−04 | −3.594E−06 | 2.180E−08 | −4.768E−11 |

Since the parameters a4, a6, a8, and a10 of the aspheric lens face F1 that should face the eye are all zero, the face F1 is a face corresponding to a conic section that has been rotated about the optical axis. The curvatures of the lens faces specified in Tables 1 and 2 lead to a parallel beam 5-1 passing through the face F0 and passing the lens 3 at its radially outermost portion making an angle α of 46° with a central beam 5-2 which passes the lens 3 along its optical axis. The beam 5-1 generates an image point 9-1 located at the edge of the field of view in the aerial image located in the image plane 7, and the beam 5-2 generates an image point 9-2 located in the center of the field of view. Thus, the ophthalmic loupe 1 of the first exemplary embodiment can image an object field with half an opening angle of 46° in the field of view. This is sufficient to at least come close to the ora serrata. The large half opening angle is achieved by virtue of a large negative distortion, i.e., a barrel distortion, being deliberately brought about in an outer region of the field of view. The negative distortion in the field of view leads to the object field now being represented with radial compression in the outer regions of the field of view, whereby object regions located further to the outside in the object field are moved closer to the center of the field of view. This allows structures of the object situated further to the outside to be imaged in the field of view.

In the present exemplary embodiment, the distortion in the innermost 45% of the field of view is zero or slightly positive, with the positive distortion not exceeding 0.55% in the present exemplary embodiment. FIG. 2 shows the curve of the distortion in the field of view of the first exemplary embodiment as a function of the radius in the field of view, which has been normalized to the maximum field of view radius. The distortion is negative in the outer 55% of the field of view, with the distortion in the outermost 80% of the field of view following a 3rd order polynomial to a very good approximation. This is evident from FIG. 3, which shows the 2nd derivative of the distortion in the field of view. It is quite evident from FIG. 3 that the 2nd derivative of the distortion in the outermost 80% of the field of view is represented by a straight line very well. The maximum negative distortion at the outermost edge of the field of view is 22.1%.

A field of view able to represent an object field located within half an opening angle of 46° can be generated by the ophthalmic loupe 1 according to the first exemplary embodiment with a very simple configuration of the ophthalmic loupe 1 and a very short installation length of the ophthalmic loupe 1 along the optical axis. The ophthalmic loupe 1 of the first exemplary embodiment has a focal length of 10.9 mm and a refractive power of 91.5 diopters.

Figure 4:
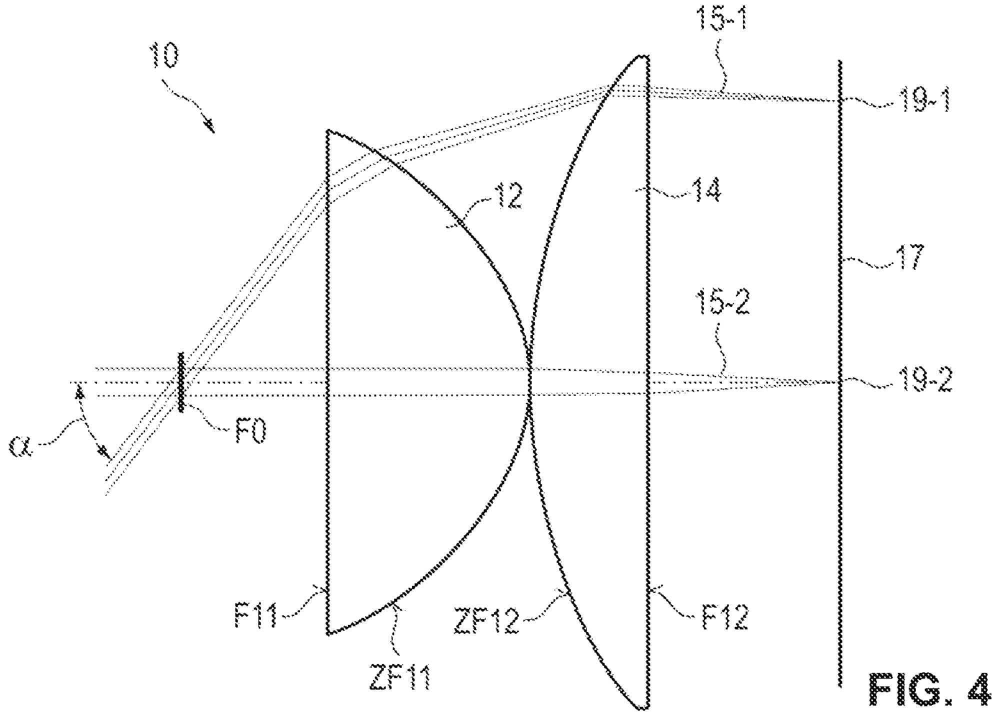
FIG. 4 shows an exemplary embodiment of an ophthalmic loupe including two lenses.
Figure 5:
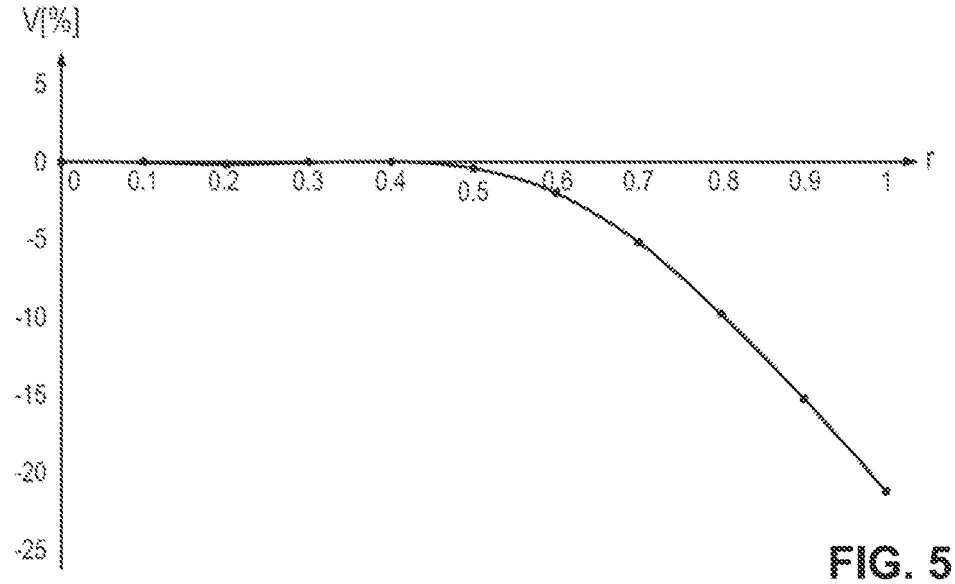
FIG. 5 shows, in the form of a diagram, the percentage distortion in the field of view generated by the ophthalmic loupe from FIG. 4, as a function of the distance from the center of the field of view.
Figure 6:
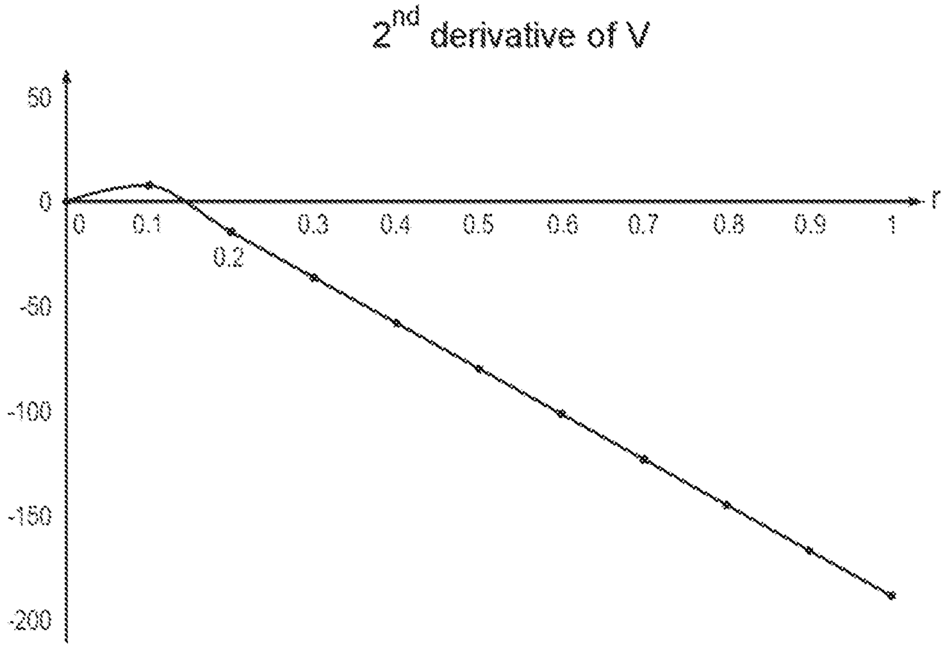
FIG. 6 shows, in the form of a diagram, the second derivative of the percentage distortion in the field of view generated by the ophthalmic loupe from FIG. 4, as a function of the distance from the center of the field of view.

An ophthalmic loupe 10 according to second exemplary embodiment of the disclosure will be described below with reference to FIGS. 4 to 6. In the second exemplary embodiment, the ophthalmic loupe 10 includes a lens system which includes two lenses 12, 14 with four lens faces F11, ZF11, ZF12, and F12. The lens face F11 should face the eye (not depicted here) when the ophthalmic loupe 10 is used. The lens face F12 forms the last lens face in front of the image plane 17 in which the aerial image is created. In the present exemplary embodiment, only the second lens face ZF11, as seen from left to right, is an aspheric face, whereas the remaining faces F11, ZF12, and F12 are spherical faces. The basic radii of curvature R of the faces F11, ZF11, ZF12, and F12, their distances from the respective next face or from the image plane 17, the glass material and the respective face diameters are summarized in Table 3. Like in the first exemplary embodiment, the face F0 represents an imaginary face, through which all imaging beams pass and which, in practice, corresponds to the pupil illuminated within the scope of the examination or treatment of the eye. The asphere coefficients a4, a6, a8, and a10 and the conic constant are specified in Table 4 for the aspheric lens face ZF11.

TABLE 3

| Face | Basic radius of curvature R [mm] | Distance [mm] | Material | Diameter [mm]: |
|---|---|---|---|---|
| F0 | inf | 5.2 | | 1 |
| F11 (SPH) | 903.527 | 7.103 | PMMA | 14.4 |
| ZF11 (ASP) | −6.521 | 0.1 | | 16.3 |
| ZF12 (SPH) | 19.513 | 4.156 | PMMA | 21.1 |
| F12 (SPH) | −811.525 | 6.957 | | 21 |

TABLE 4

| Face | k | a4 | a6 | a8 | a10 |
|---|---|---|---|---|---|
| ZF11 (ASP) | −5.068E−01 | 1.245E−04 | 8.150E−06 | −1.998E−07 | 1.705E−09 |

The curvatures of the lens faces specified in Tables 3 and 4 lead to a parallel beam 15-1 passing through the face F0 and passing the lenses 12, 14 at their radially outermost portions making an angle α of 52° with a central beam 15-2 which passes the lenses 12, 14 along their optical axes. The beam 15-1 generates an image point 19-1 located at the edge of the field of view in the aerial image located in the image plane 17, and the beam 15-2 generates an image point 19-2 located in the center of the field of view. Thus, the ophthalmic loupe 10 of the second exemplary embodiment can image an object field with half an opening angle of 52° in the field of view. This is sufficient to at least come very close to the ora serrata. The large half opening angle is achieved by virtue of a large negative distortion, i.e., a barrel distortion, being deliberately brought about in an outer region of the field of view. The negative distortion in the field of view leads to the object field now being represented with radial compression in the outer regions of the field of view, whereby object regions located further to the outside in the object field are moved closer to the center of the field of view. This allows structures of the object situated further to the outside to be imaged in the field of view.

In the present second exemplary embodiment, the distortion in the innermost 45% of the field of view is virtually zero or slightly positive or negative, with the positive or negative distortion not exceeding an absolute value of 0.2% in the present exemplary embodiment. FIG. 5 shows the curve of the distortion in the field of view of the second exemplary embodiment as a function of the radius in the field of view, which has been normalized to the maximum field of view radius. The distortion is always negative in the outer 55% of the field of view, with the distortion in the outermost 80% of the field of view following a 3rd order polynomial to a very good approximation. This is evident from FIG. 6, which shows the 2nd derivative of the distortion in the field of view. It is quite evident from FIG. 6 that the 2nd derivative of the distortion in the outermost 80% of the field of view is represented by a straight line very well. The maximum negative distortion at the outermost edge of the field of view is 21%.

A field of view able to represent an object field located within half an opening angle of 52° can be generated by the ophthalmic loupe 10 according to the second exemplary embodiment with a still simple configuration of the ophthalmic loupe 10 and a still compact installation length of the ophthalmic loupe 10 along the optical axis. The ophthalmic loupe 10 of the second exemplary embodiment has a focal length of 9.85 mm and a refractive power of 101.6 diopters.

As a result of radii of curvature whose absolute values are larger than 900 or larger than 800 mm, the two outer faces F11 and F12 of the ophthalmic loupe 10 of the second exemplary embodiment have very large radii of curvature, and this leads to largely plane faces, which have in each case slightly convex curvatures as seen from outside of the lens in the present exemplary embodiment. Hence, the ophthalmic loupe 10 not attaching to the eye with the face F11 in the case of inadvertent contact with the eye and no liquid being able to collect on the face F12, which faces the image plane 17 and which generally faces upward when the ophthalmic loupe 10 is used, is ensured in the present exemplary embodiment.

Figure 7:
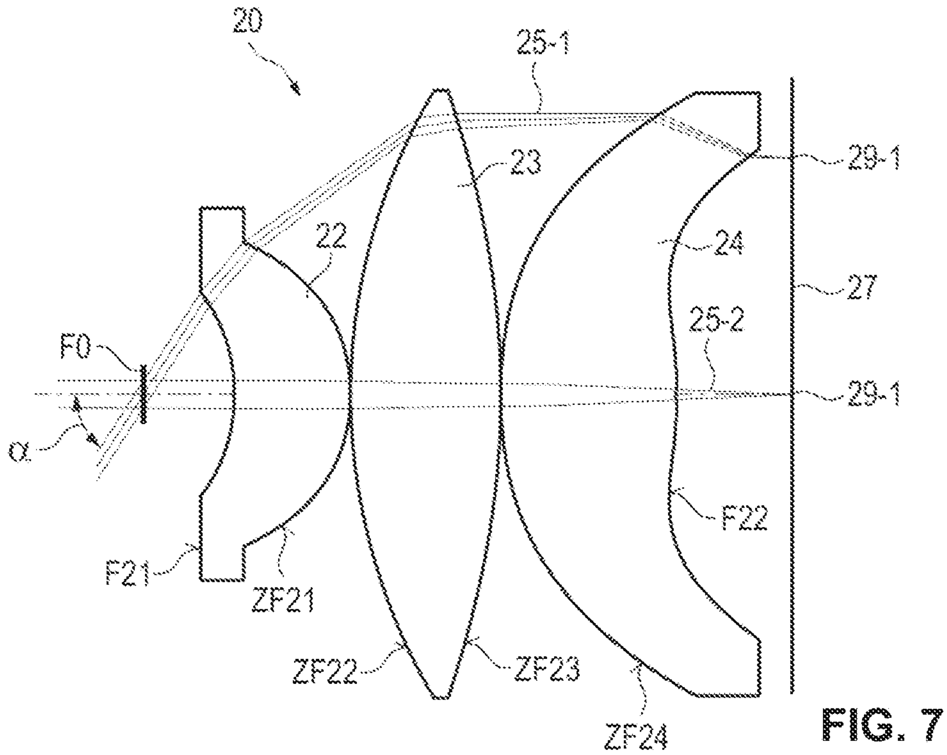
FIG. 7 shows an exemplary embodiment of an ophthalmic loupe including three lenses.
Figure 8:
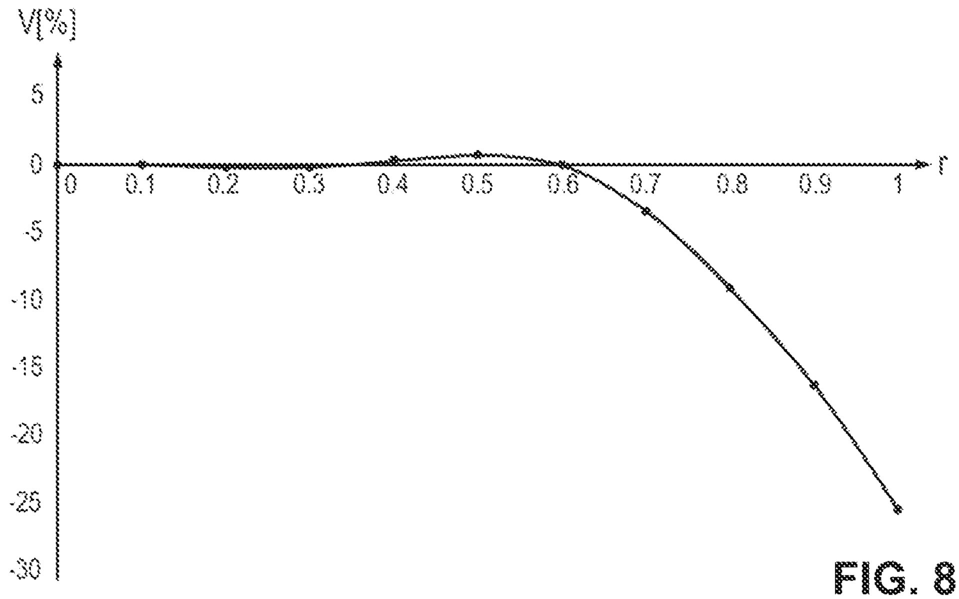
FIG. 8 shows, in the form of a diagram, the percentage distortion in the field of view generated by the ophthalmic loupe from FIG. 7, as a function of the distance from the center of the field of view.
Figure 9:
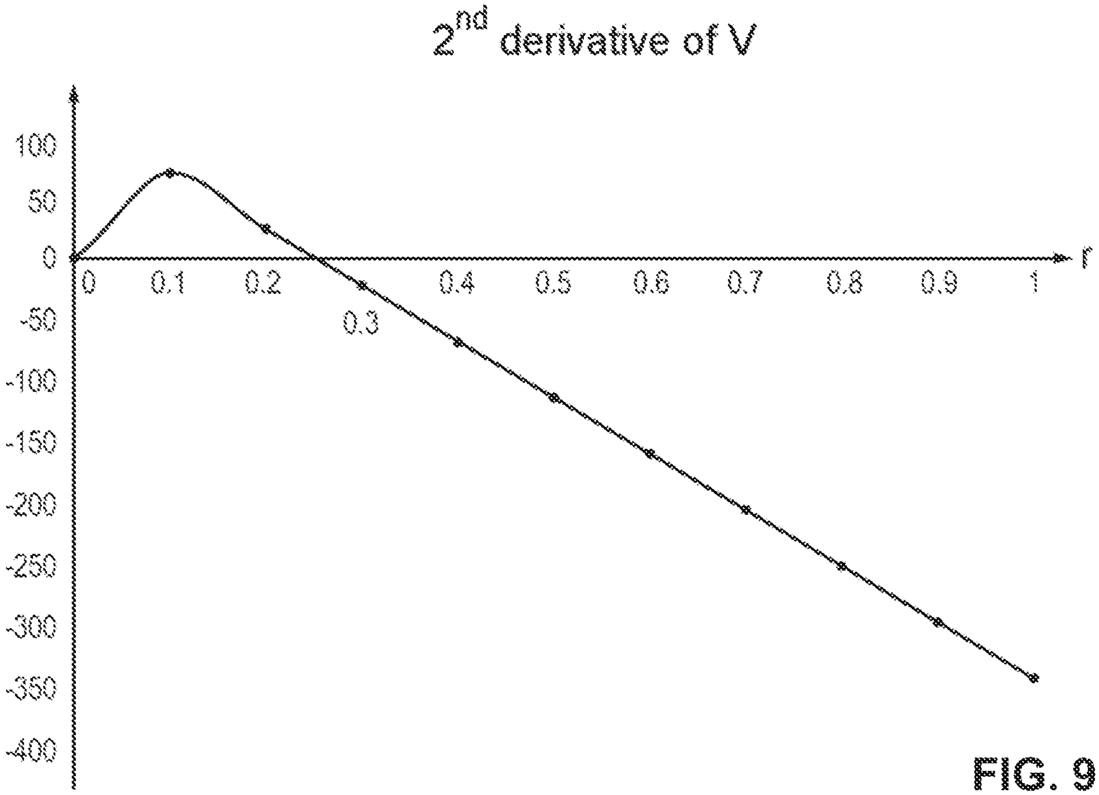
FIG. 9 shows, in the form of a diagram, the second derivative of the percentage distortion in the field of view generated by the ophthalmic loupe from FIG. 7, as a function of the distance from the center of the field of view.

A third exemplary embodiment of an ophthalmic loupe 20 according to an aspect of the disclosure will be described below with reference to FIGS. 7 to 9. In the third exemplary embodiment, the ophthalmic loupe 20 includes a lens system which includes three lenses 22, 23, and 24 with six lens faces F21, ZF21, ZF22, ZF23, ZF24, and F22 in total. The lens face F21 should face the eye (not depicted here) when the ophthalmic loupe 20 is used. The lens face F22 forms the last lens face in front of the image plane 27 in which the aerial image is created. In the present exemplary embodiment, the last two lens faces ZF24 and F22, as seen from left to right, are aspheric faces. The remaining faces F21, ZF21, ZF22, and ZF23 are spherical faces. The basic radii of curvature R of the faces F21, ZF21, ZF22, ZF23, ZF24, and F22, their distances from the respective next face or from the image plane 27, the glass material and the respective face diameters are summarized in Table 5. Like in the first two exemplary embodiments, the face F0 represents an imaginary face, through which all imaging beams pass and which, in practice, corresponds to the pupil illuminated within the scope of the examination or treatment of the eye. The asphere coefficients a4, a6, a8, and a10 and the conic constant are specified in Table 6 for the aspheric lens faces ZF24 and F22.

TABLE 5

| Face | Basic radius of curvature R [mm] | Distance [mm] | Material | Diameter [mm]: |
|---|---|---|---|---|
| F0 | inf | 4.4 | | 1 |
| F21 (SPH) | −7.895 | 5.72 | LBAL35 (OHARA) | 9.6 |
| ZF21 (SPH) | −7.784 | 0.1 | | 14.7 |
| ZF22 (SPH) | 29.512 | 7.254 | LBAL35 (OHARA) | 27.1 |
| ZF23 (SPH) | −43.599 | 0.1 | | 27.5 |
| ZF24 (ASP) | 22.709 | 8.496 | PMMA | 27.5 |
| F22 (ASP) | −19.862 | 5.71 | | 23.5 |

TABLE 6

| Face | k | a4 | a6 | a8 | a10 |
|---|---|---|---|---|---|
| ZF24 (ASP) | 3.216E−01 | 6.890E−05 | 2.153E−07 | −8.170E−10 | 0 |
| F22 (ASP) | 1.610E+00 | 3.924E−04 | 3.554E−06 | −4.201E−08 | 1.504E−10 |

The curvatures of the lens faces specified in Tables 5 and 6 lead to a parallel beam 25-1 passing through the face F0 and passing the lenses 22, 23, and 24 at their radially outermost portions making an angle $\alpha$ of 57° with a central beam 25-2 which passes the lenses 22, 23, and 24 along their optical axes. The beam 25-1 generates an image point 29-1 located at the edge of the field of view in the aerial image located in the image plane 27, and the beam 25-2 generates an image point 29-2 located in the center of the field of view. Thus, the ophthalmic loupe 20 of the third exemplary embodiment can image an object field with half an opening angle of 57° in the field of view. This is sufficient to represent the ora serrata. The very large half opening angle is achieved by virtue of a large negative distortion, i.e., a barrel distortion, being deliberately brought about in an outer region of the field of view. The negative distortion in the field of view leads to the object field now being represented with radial compression in the outer regions of the field of view, whereby object regions located further to the outside in the object field are moved closer to the center of the field of view. This allows structures of the object situated further to the outside to be imaged in the field of view.

In the present third exemplary embodiment, the distortion in the innermost 60% of the field of view is virtually zero or slightly positive or negative, with the positive or negative distortion not exceeding an absolute value of 0.4% in the present exemplary embodiment. FIG. 8 shows the curve of the distortion in the field of view of the third exemplary embodiment as a function of the radius in the field of view, which has been normalized to the maximum field of view radius. The distortion is always negative in the outer 40% of the field of view, with the distortion in the outermost 80% of the field of view following a 3rd order polynomial to a very good approximation. This is evident from FIG. 9, which shows the 2nd derivative of the distortion in the field of view. It is quite evident from FIG. 9 that the 2nd derivative of the distortion in the outermost 80% of the field of view is represented by a straight line very well. The maximum negative distortion at the outermost edge of the field of view is 26.1%.

A field of view able to represent an object field located within a very large half an opening angle of 57° can be generated by the ophthalmic loupe 20 according to the third exemplary embodiment with a still acceptable complexity of the ophthalmic loupe 20 and a still acceptable installation length of the ophthalmic loupe 20 along the optical axis. The ophthalmic loupe 20 of the third exemplary embodiment has a focal length of 10.2 mm and a refractive power of 98.1 diopters.

Figure 10:
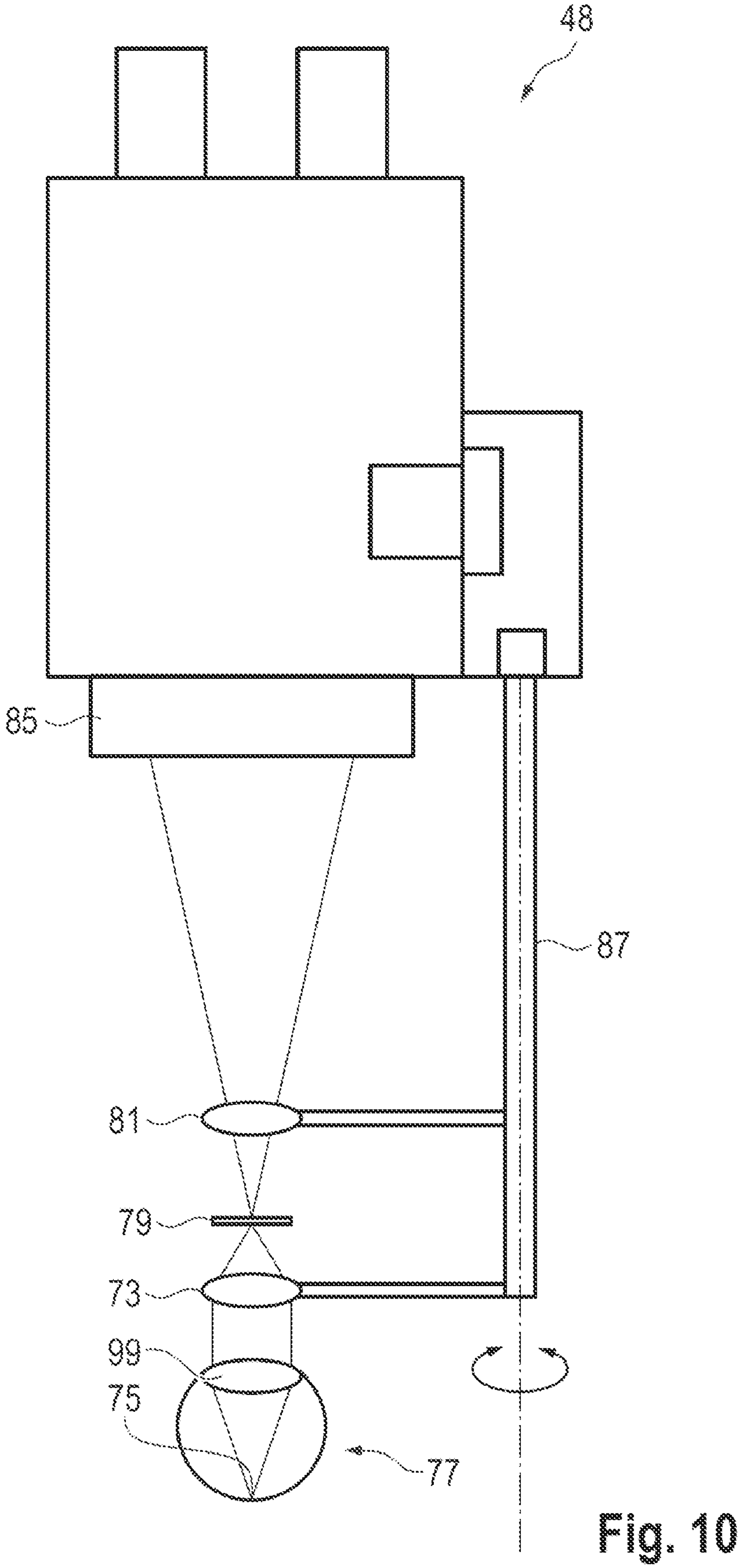
FIG. 10 shows an exemplary embodiment of an optical imaging system having a surgical microscope and an ophthalmic loupe.

An exemplary embodiment of an optical imaging system having a surgical microscope 48 and having an ophthalmic loupe 73 according to an aspect of the disclosure will be described below on the basis of FIG. 10. The fundus 75 of an eye 77 can be projected into an intermediate image plane 79 as an aerial image with the aid of the ophthalmic loupe 73 arranged on a pivoting system 87 which allows the latter to be pivoted into the observation beam path of the surgical microscope 48. The aerial image situated in the intermediate image plane 79 is then observed under magnification using the surgical microscope 48.

The surgical microscope 48 typically has an ergonomic configuration for a working distance from the eye 77 at which it images the anterior eye segment 99 in focus. If the ophthalmic loupe 73 is now pivoted into the beam path, the surgical microscope 48 must image the aerial image formed by the ophthalmic loupe 73 in the intermediate image plane 79 in focus rather than the anterior eye segment 99. If the surgical microscope 48 has a main objective 85 with a fixed focal length, the surgical microscope 48 can for example be positioned at a further distance from the eye 77 such that its distance from the intermediate image plane 79 corresponds to the front focal distance of its main objective 85, in order to generate a sharp image representation of the aerial image situated in the intermediate image plane 79. However, a different procedure has been chosen in the present exemplary embodiment. An optical group 81 is also arranged on the pivoting system 87, on which the ophthalmic loupe 73 is arranged, and, together with the main objective 85, said optical group forms a lens system whose front focal distance corresponds exactly to the distance between the object-side vertex of the intermediate image-side last element of the optical group 81 and the intermediate image plane 79. By pivoting-in this optical group 81 at the same time as and together with the ophthalmic loupe 73, it is possible to change from an observation of the anterior eye segment 99 to an observation of the fundus 75 of the eye without needing to modify the working position of the surgical microscope 48 in relation to the eye 77. Especially if the ophthalmic loupe 73 includes merely a single lens, the optical group 81 can additionally or alternatively also serve the correction of chromatic aberrations of the ophthalmic loupe 73. Unlike what is depicted in FIG. 10, the optical group 81 can also be arranged closer to the main objective 85, wherein its diameter must then be increased accordingly in comparison with the illustration in FIG. 10.

Should the surgical microscope 48 have a main objective with a variable focal length rather than a main objective 85 with a fixed focal length, it is also possible, without the use of an optical group 81, to modify the front focal distance of the main objective while maintaining the working position of the surgical microscope 48 in relation to the eye 77 such that there is a switch from focusing on the anterior eye segment 99 to focusing on the intermediate image situated in the intermediate image plane 79. The optical group 81 can then be dispensed with or only serve the correction of a chromatic aberration of the ophthalmic loupe 73, especially if the ophthalmic loupe 73 includes a single lens. Both the optical group 81 and a main objective with a variable focal length allow a switchover from an observation of the anterior eye segment 99 to an observation of the fundus 75 of the eye without needing to increase the working distance of the surgical microscope 48 from the eye 77, as this would entail the acceptance of economic disadvantages.

The present disclosure has been described in detail on the basis of exemplary embodiments for explanatory purposes. However, a person skilled in the art recognizes that there can be deviations from these exemplary embodiments within the scope of the disclosure. Therefore, the disclosure is not intended to be limited by the exemplary embodiments but rather only by the appended claims.

LIST OF REFERENCE NUMERALS

1 Ophthalmic loupe
3 Lens
5-1 Beam
5-2 Beam
7 Image plane
9-1 Image point
9-2 Image point
10 Ophthalmic loupe
12 Lens
14 Lens
15-1 Beam
15-2 Beam
17 Image plane
19-1 Image point
19-2 Image point
20 Ophthalmic loupe
22 Lens
23 Lens
24 Lens
25-1 Beam
25-2 Beam
27 Image plane
29-1 Image point
29-2 Image point
F0 Face
F1 Lens face
F2 Lens face
F11 Lens face
F12 Lens face
F21 Lens face
F22 Lens face
ZP11 Lens face
ZF12 Lens face
ZF21 Lens face
ZF22 Lens face
ZF23 Lens face
ZF24 Lens face

48 Surgical microscope
73 Ophthalmic loupe
75 Eye fundus
77 Eye
79 Intermediate image plane
81 Optical group
85 Main objective
87 Pivoting system
99 Anterior eye segment

What is claimed is:

1. An ophthalmic loupe for generating an aerial image of a portion of an eye, the ophthalmic loupe comprising:

at least one lens having at least two lens faces, wherein at least one of the at least two lens faces is an aspheric lens face which in combination with a remaining lens face or remaining lens faces of the at least one lens generates an aerial image of the portion of the eye with a field of view with a negative distortion in its outer region, wherein an absolute value of the negative distortion at an edge of the field of view is larger than 15%, wherein the aspheric lens face generates an aerial image in which at least an outer 40% of the field of view has a negative distortion, and wherein the aspheric lens face leads to the negative distortion which, at least in the outer 40% of the field of view, increases more than proportionally in a direction of the edge of the field of view and can be described by a polynomial V(r) whose second derivative is negative.

2. The ophthalmic loupe according to claim 1, wherein the aspheric lens face generates an aerial image in which at most an innermost 60% of the field of view has no distortion or a positive distortion, and wherein the positive distortion has a maximum absolute value of less than 0.75%.

3. The ophthalmic loupe according to claim 1, wherein a second derivative of the polynomial V(r) can be approximated by a straight line with a coefficient of determination of at least R2>99%, and wherein r describes a distance of a field point in the field of view from the center of the field of view, normalized to the maximum radius of the field of view.

4. The ophthalmic loupe according to claim 1, wherein the ophthalmic loupe is configured as a lens system which includes at least two lenses.

5. The ophthalmic loupe according to claim 1, wherein the ophthalmic loupe is configured as a lens system which includes no more than three lenses.

6. The ophthalmic loupe according to claim 4, wherein the lens system includes a first lens configured to form an eye-side end of the lens system when the ophthalmic loupe is used and a second lens configured to form an aerial image-side end of the lens system when the ophthalmic loupe is used, wherein the first lens includes a first lens face facing the eye when the ophthalmic loupe is used, wherein the second lens includes a second lens face forming the last lens face in front of the aerial image when the ophthalmic loupe is used, and wherein at least one of the first lens face has a radius of curvature of at least 100 mm and the second lens face has a radius of curvature of at least 100 mm.

7. The ophthalmic loupe according to claim 6, wherein the first lens face has a radius of curvature of at least 200 mm.

8. The ophthalmic loupe according to claim 1, wherein the ophthalmic loupe has a refractive power of at least 90 diopters.

9. The ophthalmic loupe according to claim 1, wherein no more than two aspheric lens faces are present.

10. The ophthalmic loupe according to claim 9, wherein all other lens faces are spherical lens faces.

11. The ophthalmic loupe according to claim 1, wherein two aspheric lens faces are present, and wherein the two aspheric lens faces are lens faces of a same lens.

12. A lens combination to be arranged between a main objective of a surgical microscope and an eye, the lens combination comprising:

an ophthalmic loupe according to claim 1 which faces the eye and which is configured to generate an aerial image of a portion of the eye in an intermediate image plane; and an optical group which faces the main objective, which includes at least one lens, wherein the optical group is configured to at least one of (1) displace a focal point of the main objective into the intermediate image plane and (2) compensate for chromatic aberrations of the ophthalmic loupe.

13. An optical imaging system comprising:

a surgical microscope with an observation beam path and a focal point of the observation beam path; and the ophthalmic loupe according to claim 1 which is introducible into the observation beam path of the surgical microscope such that the aerial image of the ophthalmic loupe is located at the focal point of the observation beam path.

14. The optical imaging system according to claim 13, wherein the ophthalmic loupe is a part of a lens combination which is introducible into the observation beam path of the surgical microscope, and wherein the lens combination includes:

the ophthalmic loupe which faces the eye and which is configured to generate an aerial image of a portion of the eye in an intermediate image plane; and an optical group which faces the main objective, which includes at least one lens, wherein the optical group is configured to at least one of (1) displace a focal point of the main objective into the intermediate image plane and (2) compensate for chromatic aberrations of the ophthalmic loupe.

15. The ophthalmic loupe according to claim 1, wherein the aspheric lens face in combination with the remaining lens face or the remaining lens faces generates an aerial image in which at least an outer 40% of the field of view has the negative distortion.

16. The ophthalmic loupe according to claim 1, wherein the aspheric lens face in combination with the remaining lens face or the remaining lens faces generates an aerial image in which at most an innermost 60% of the field of view has no distortion or a positive distortion, and wherein the positive distortion has a maximum absolute value of less than 0.75%.

17. The ophthalmic loupe according to claim 1, wherein the aspheric lens face in combination with the remaining lens face or the remaining lens faces leads to a negative distortion which, at least in the outer 40% of the field of view, increases more than proportionally in a direction of the edge of the field of view.

18. The ophthalmic loupe according to claim 1, wherein the aspheric lens face in combination with the remaining lens face or the remaining lens faces leads to a distortion which, in the outer 40% of the field of view, can be described by the polynomial V(r) whose second derivative can be approximated by a straight line with a coefficient of determination of at least R2>99%, and wherein r describes a distance of a field point in the field of view from the center of the field of view, normalized to the maximum radius of the field of view.

* * * * *